United States Patent [19]
Halberstadt

[11] Patent Number: 6,034,068
[45] Date of Patent: *Mar. 7, 2000

[54] LAMININ 5 FOR PERIODONTAL TREATMENT

[75] Inventor: Craig Halberstadt, San Diego, Calif.

[73] Assignee: Desmos, Incorporated, San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/059,849

[22] Filed: Apr. 14, 1998

Related U.S. Application Data

[63] Continuation of application No. 08/625,050, Mar. 29, 1996, abandoned.

[51] Int. Cl.⁷ .............................. A61K 38/00; A61F 2/02; A61F 2/10; A61F 13/00
[52] U.S. Cl. .......................... 514/21; 424/422; 435/325; 435/366; 435/41; 435/402; 514/2; 514/12; 514/801; 530/350; 530/395; 623/11; 623/15
[58] Field of Search ............................ 424/422; 435/325; 435/366, 41, 402; 530/350, 395; 623/15, 11; 514/2, 801, 12, 21

[56] References Cited

U.S. PATENT DOCUMENTS

| | | |
|---|---|---|
| 4,870,160 | 9/1989 | Charonis et al. . |
| 5,092,885 | 3/1992 | Yamada et al. . |
| 5,266,328 | 11/1993 | Skubitz et al. . |
| 5,422,264 | 6/1995 | Quaranta et al. . |
| 5,489,300 | 2/1996 | Capecchi et al. . |
| 5,510,263 | 4/1996 | Quaranta et al. . |
| 5,541,106 | 7/1996 | Jones . |
| 5,585,267 | 12/1996 | Jones et al. . |
| 5,656,593 | 8/1997 | Kuberasampath et al. ................ 514/12 |
| 5,672,361 | 9/1997 | Halberstadt et al. ................... 424/93.7 |
| 5,770,448 | 6/1998 | Jones et al. ............................. 435/325 |

FOREIGN PATENT DOCUMENTS

| | | |
|---|---|---|
| 4040872 | 7/1992 | Germany . |
| WO 89/01493 | 2/1989 | WIPO . |
| WO 90/05741 | 5/1990 | WIPO . |
| WO 90/13566 | 11/1990 | WIPO . |
| WO 92/17498 | 10/1992 | WIPO . |
| WO 94/05316 | 3/1994 | WIPO . |
| WO 94/23016 | 10/1994 | WIPO . |
| WO 95/06660 | 3/1995 | WIPO . |

OTHER PUBLICATIONS

Haapasalmi et al. Am. J. Pathol. vol. 147 (1), pp. 193–206, 1995.
W.G. Carter, et al., Epiligrin, A New Cell Adhesion Ligand For Intergrin α3β1 in Epithelial Basement Membranes, *Cell,*, 65:599–610, (1991).
Champliaud et al., *J. Cell Biol.,* 132(6):1189–1198, Abstract, Mar. 1996.
K. Garrison, et al., *Drosophila* Laminin A Chain Sequence, Interspecies Comparison, and Domain Structure of a Major Carboxyl Portion, *J. Biol. Chem.,* 266(34):22899–22904 (1991).
Y. Hieda, et al., Identification of a New Hemidesmosomal Protein, HD1: A Major, High Molecular Mass Component of Isolated Hemidesmosomes, *J. Cell Biol.,* 116(6):1497–1506 (1992).
B. Hsi, et al., Monoclonal Antibody $GB_36$ Raised Against Human Trophoblast Recognizes a Novel Epithelial Antigen, *Placenta,,* 8:209–217 (1987).
K. Izumi, et al., In Vitro Induction of Ornithine Decarboxylase in Urinary Bladder Carcinoma Cells, *Cancer Research,* 41:405–409 (1981).
P. Kallunki, et al., A Truncated Laminin chain Homologous to the B2 Chain: Structure, Spatial Expression, and Chromosomal Assignment, *J. Cell Biol,* 119(3):679–693, (1992).
M. Langhofer, et al., The Matrix Secreted by 804G Cells Contains Laminin–Related Components that Participate in Hemidesmosome Assembly in Vitro, *J. Cell Science,* 105:753–764, (1993).
Nishiyama, et al., Annual Meeting *Soc. Invest. Dermatol.,,* Abstract May 1995.
Nishiyama, et al., 34th Annual Meeting *Am. Soc. Cell Biol.,* Abstract 1994.
K.S. Riddelle, et al., Formation of Hemidesmosomes in Vitro By a Transformed Rat Bladder Cell Line, *J. Cell Biol.,* 112(1):159–168 (1991).
K.S. Riddelle, et al., Hemidesmosomes in the Epithelial Cell Line 804G: Their Fate During Wound Closure, Mitosis and Drug Induced Reorganization of the Cytoskeleton, *J. Cell Science,* 103:475–490 (1992).
P. Rousselle, et al., Kalinin: An Epithelium–Specific Basement Membrane Adhesion Molecule that is a Component of Anchoring Filaments, *I/. Cell Biol.* 114(3):567–576 (1991).
L.A. Staehelin, Structure and Function of Intercellular Junctions, *Dept. of Molecular, Cellular and Developmental Biology,* Univ. of Colorado, Boulder, Colorado, 191–283 (1974).
P. Verrando, et al., The New Basement Membrane Antigen Recognized by the Monoclonal Antibody GB3 is a Large Size Glycoprotein: Modulation of its Expression by Retinoic Acid, *Biochimica et Biophysica Acta,* 942:45–56 (1988).

*Primary Examiner*—Leon B. Lankford, Jr.
*Assistant Examiner*—Christopher R. Tate
*Attorney, Agent, or Firm*—Knobbe, Martens, Olson & Bear, LLP.

[57] ABSTRACT

A trans-epithelial appliance or shaped article coated with laminin 5. Laminin 5 stimulates cell attachment and may be comprise an insoluble or soluble cell matrix. The appliance will be useful for reducing inflammation and/or infection at the site of entry of the appliance. The appliance may also be used to stimulate gum junctional epithelium adhesion in the treatment of, for example, gingivitis and periodontitis.

10 Claims, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 295 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
      (B) CLONE: 150 kD (xi) SEQUENCE DESCRIPTION: SEQ ID NO:1:

```
Glu Phe Glu Thr Leu Gln Glu Lys Ala Gln Val Asn Ser Arg Lys Ala
1               5                   10                  15

Gln Thr Leu Tyr Asn Asn Ile Asp Thr Thr Ile Gln Asn Ala Lys Glu
            20                  25                  30

Leu Asp Met Lys Ile Lys Asn Ile Leu Thr Asn Val His Ile Leu Leu
        35                  40                  45

Lys Gln Ile Ala Arg Pro Gly Gly Glu Gly Met Asp Leu Pro Val Gly
    50                  55                  60

Asp Trp Ser Arg Glu Ser Ala Glu Arg His Gly His Val Ala Glu Ser
65                  70                  75                  80

Arg Gly Arg Asp Phe Lys Lys His Leu Gln Glu Ala Glu Ala Gln Lys
                85                  90                  95

Met Glu Ala Gln Leu Leu Leu Asn Arg Ile Arg Thr Trp Leu Glu Ser
                100                 105                 110

His Gln Val Glu Asn Asn Gly Leu Leu Lys Asn Ile Arg Asp Ser Leu
            115                 120                 125

Asn Asp Tyr Glu Ala Lys Leu Gln Asp Leu Arg Ser Val Leu Gln Glu
        130                 135                 140

Ala Ala Ala Gln Gly Lys Gln Ala Thr Gly Leu Asn His Glu Asn Glu
145                 150                 155                 160

Gly Val Leu Gly Ala Ile Gln Arg Gln Met Lys Glu Met Asp Ser Leu
                165                 170                 175

Lys Lys Tyr Leu Thr Glu His Leu Ala Thr Ala Asp Ala Ser Leu Leu
            180                 185                 190

Gln Thr Asn Ser Leu Leu Gln Arg Met Asp Thr Ser Gln Lys Glu Tyr
        195                 200                 205

Glu Ala Trp Gln Ile Asp Ile Ser Leu Glu Gln His Pro Val His Asn
    210                 215                 220
```

```
Cys Leu Leu Arg Leu Thr Leu Arg Gln Asp Leu Ile Asp Leu Asn Phe
225                 230                 235                 240

Ser Phe Ser Val Pro Gln Val Val Asp Thr Arg Gln Leu Ala Ile Tyr
            245                 250                 255

Asn Arg His Ala Tyr Val Val Leu Gly Gly Ile Leu Val Ser Lys Val
            260                 265                 270

His Tyr Lys His Cys Pro Thr Cys Leu His Ser Leu Leu Ser Leu Val
        275                 280                 285

Phe Gly Gly Thr Lys Thr Tyr
290                 295

(2) INFORMATION FOR SEQ ID NO:2:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: laminin A (xi) SEQUENCE DESCRIPTION: SEQ ID NO:2:

Lys Phe Asp Thr Val Ser Glu Gln Lys Leu Gln Ala Glu Lys Asn Ile
1               5                   10                  15

Lys Asp Ala Gly Asn Phe Leu Ile Asn Gly Asp Leu Thr Leu Asn Gln
            20                  25                  30

Ile Asn Gln Lys Leu Asp Asn Leu Arg Asp Ala Leu Asn Glu Leu Asn
            35                  40                  45

Ser Phe Asn Lys Asn Val Asp Glu Glu Leu Pro Val Arg Glu Asp Gln
50                  55                  60

His Lys Glu Ala Asp Ala Leu Thr Asp Gln Ala Glu Gln Lys Ala Ala
65                  70                  75                  80

Glu Leu Ala Ile Lys Ala Gln Asp Leu Ala Ala Gln Tyr Thr Asp Met
                85                  90                  95

Thr Ala Ser Ala Glu Pro Ala Ile Lys Ala Ala Thr Ala Tyr Ser Gly
            100                 105                 110

Ile Val Glu Ala Val Glu Ala Ala Gln Lys Leu Ser Gln Asp Ala Ile
            115                 120                 125

Ser Ala Ala Gly Asn Ala Thr Asp Lys Thr Asp Gly Ile Glu Glu Arg
130                 135                 140

Ala His Leu Ala Asp Thr Gly Ser Thr Asp Leu Leu Gln Arg Ala Arg
145                 150                 155                 160

Gln Ser Leu Gln Lys Val Gln Asp Asp Leu Glu Pro Arg Leu Asn Ala
                165                 170                 175

Ser Ala Gly Lys Val Gln Lys Ile Ser Ala Val Asn Asn Ala Thr Glu
            180                 185                 190

His Gln Leu Lys Asp Ile Asn Lys Leu Ile Asp Gln Leu Pro Ala Glu
            195                 200                 205

Ser Gln Arg Asp Met Trp Lys Asn Ser Asn Ala Asn Ala Ser Asp Glu
210                 215                 220
```

```
Ala Glu Ile Leu Lys Asn Val Leu Glu Ile Leu Glu Pro Val Ser Val
225                 230                 235                 240

Gln Thr Pro Lys Glu Leu Glu Lys Ala His Gly Ile Asn Arg Asp Leu
            245                 250                 255

Asp Leu Thr Asn Lys Asp Val Ser Gln Ala Asn Lys Gln Leu Asp Asp
                260                 265                 270

Val Glu Gly Ser Val Ser Lys Leu Asn Glu Leu Ala Glu Asp Ile Glu
            275                 280                 285

Glu Gln Gln His Arg Val Gly Ser Gln Ser Arg Gln Leu Gly Gln Glu
            290                 295                 300

Ile Glu Asn Leu Lys Ala Gln Val Glu Ala Ala Arg Gln Leu Ala Asn
305                 310                 315                 320

Ser Ile Lys Val Gly Val Asn Phe Lys Pro Ser Thr Ile Leu Glu Leu
                325                 330                 335

Lys Thr Pro Glu Lys Thr Lys Leu Leu Ala Thr Arg Thr Asn Leu Ser
            340                 345                 350

Thr Tyr Phe Arg Thr Thr Glu Pro
            355                 360
```

(2) INFORMATION FOR SEQ ID NO:3:

(i) SEQUENCE CHARACTERISTICS:
        (A) LENGTH: 337 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: merosin (xi) SEQUENCE DESCRIPTION: SEQ ID NO:3:

```
Glu Leu Lys His Leu Leu Ser Pro Gln Arg Ala Pro Glu Arg Leu Ile
1               5                   10                  15

Gln Leu Ala Glu Gly Asn Leu Asn Thr Leu Val Thr Glu Met Asn Glu
            20                  25                  30

Leu Leu Thr Arg Ala Thr Lys Val Thr Ala Asp Gly Glu Gln Thr Gly
            35                  40                  45

Gln Asp Ala Glu Arg Thr Asn Thr Arg Ala Lys Ser Leu Gly Glu Phe
    50                  55                  60

Ile Lys Glu Leu Ala Arg Asp Ala Glu Ala Val Asn Glu Lys Ala Ile
65                  70                  75                  80

Lys Leu Asn Glu Thr Leu Gly Thr Arg Asp Glu Ala Phe Glu Arg Asn
                85                  90                  95

Leu Glu Gly Leu Gln Lys Glu Ile Asp Gln Met Ile Lys Glu Leu Arg
            100                 105                 110

Arg Lys Asn Leu Glu Thr Gln Lys Glu Ile Ala Glu Asp Glu Leu Val
            115                 120                 125

Ala Ala Glu Ala Leu Leu Lys Lys Val Lys Lys Leu Phe Gly Glu Ser
            130                 135                 140

Arg Gly Glu Asn Glu Glu Met Glu Lys Asp Leu Arg Glu Lys Leu Ala
145                 150                 155                 160
```

```
Asp Tyr Lys Asn Lys Val Asp Asp Ala Trp Asp Leu Leu Arg Glu Ala
            165                 170                 175

Thr Asp Lys Ile Arg Glu Ala Asn Arg Leu Phe Ala Val Asn Gln Lys
            180                 185                 190

Asn Met Thr Ala Leu Glu Lys Lys Lys Glu Ala Val Glu Ser Gly Lys
        195                 200                 205

Arg Gln Ile Glu Asn Thr Leu Lys Glu Gly Asn Asp Ile Leu Asp Glu
        210                 215                 220

Ala Asn Arg Leu Ala Asp Glu Ile Asn Ser Ile Ile Asp Tyr Val Glu
225                 230                 235                 240

Asp Ile Gln Thr Lys Leu Pro Pro Met Ser Glu Glu Leu Asn Asp Lys
                245                 250                 255

Ile Asp Asp Leu Ser Gln Glu Ile Lys Asp Arg Lys Leu Ala Glu Lys
                260                 265                 270

Val Ser Gln Ala Glu Ser His Ala Ala Gln Leu Asn Asp Ser Ser Ala
        275                 280                 285

Val Leu Asp Gly Ile Leu Asp Glu Ala Lys Asn Ile Ser Phe Asn Ala
        290                 295                 300

Thr Ala Ala Phe Lys Ala Tyr Ser Asn Ile Lys Asp Tyr Ile Asp Glu
305                 310                 315                 320

Ala Glu Lys Val Ala Lys Glu Ala Lys Asp Leu Ala His Glu Ala Thr
                325                 330                 335

Lys
```

LAMININ 5 FOR PERIODONTAL TREATMENT

This application is a continuation in part of Ser. No. 08/625,050 filed Mar. 29, 1996 now abandoned.

FIELD OF THE INVENTION

The present invention relates to the attachment of cells to shaped articles. More specifically, the invention relates to the attachment of epithelial cells to laminin 5-coated biologically compatible implants and trans-epithelial appliances.

BACKGROUND OF THE INVENTION

When organs of the body are formed, they develop in neatly organized arrays. Often, cell types are separated by connective tissue called basement membranes. In skin, for instance, the superficial layer of epidermal cells adheres to the underlying basement membrane. This skin basement membrane acts as a barrier between the epidermal cells on the outside, and the dermal cells underneath. A similar arrangement of cells occurs in the lining of the gut and in the oral cavity.

Basement membranes have been implicated in the growth, attachment, migration, repair and differentiation of their overlying cell populations. Three layers have been defined in basement membranes: a) the lamina lucida, an electronmicroscopically clear region in close approximation to the overlying cells; b) the lamina densa, an electron dense region of 20–300 nm in width; and c) the sublamina densa which contains anchoring fibrils, microfibrillar bundles and collagen fibers.

Many epithelial cells interact with the underlying extracellular matrix, a network of proteins to which cells attach, via a junction called the hemidesmosome (Staehelin, (1974) *Structure and Function of Intercellular Junctions,* Department of Molecular, Cellular and Developmental Biology, University of Colorado, Boulder, Colo., 191–283). The hemidesmosome, with its anchored structures including intermediate filaments and anchoring fibrils, forms an adhesion complex.

When cultured on tissue culture plastic in vitro, most epithelial cells do not assemble bona fide hemidesmosomes despite the fact that they appear to express all of the necessary plaque and hemidesmosomal components. Several cell lines, including the 804G and NBT-II rat bladder carcinoma cell lines, are capable of assembling hemidesmosomes in vitro under standard culture conditions (Riddelle et al., (1991) *J. Cell Biol.,* 112:159–168; Hieda et al., (1992), *J. Cell Biol.,* 116:1497). It has also been reported that substratum-induced staining by anti-hemidesmosome antibodies is greatly diminished in 804G cell cultures that enter in vitro wound sites (Riddelle et al., (1992) *J. Cell Sci.,* 103:475–490).

As described in Langhofer et al. (1993) *J. Cell Sci.,* 105:753–764) and in copending allowed application Ser. No. 08/324,367 U.S. Pat. No. 5,547,106, the entire contents of which are hereby incorporated by reference, when epithelial cells unable to themselves form hemidesmosomes are plated on the cell matrix deposited by 804G or NBT-II rat bladder carcinoma cells, hemidesmosome formation is induced.

In addition, U.S. Pat. No. 5,422,264, the entire contents of which are hereby incorporated by reference, discloses that a soluble matrix equivalent produced by 804G cells can also induce attachment and hemidesmosome formation in cells contacted with the soluble matrix. The 804G deposited (insoluble) matrix and soluble matrix contain similar protein components as visualized by immunoblotting. These proteins exhibit significant similarity to human merosin, a laminin A isoform, and to Drosophila laminin A. Allowed copending U.S. application Ser. No. 08/152,460 U.S. Pat. No. 5,510,263, the entire contents of which are hereby incorporated by reference, discloses the enhanced growth of pancreatic islet cells cultured on the 804G deposited matrix.

Molecules structurally similar, if not identical to the 804G matrix are also produced by human cell lines; however, these molecules have not been observed to induce hemidesmosome formation in cells plated thereon. Rouselle et al. (*J. Cell Biol.,* 114:567–576, 1991; Burgeson et al., PCT WO92/17498 and PCT WO94/05316) describe a molecule called kalinin which is secreted into the culture medium by human keratinocytes and enhances keratinocyte cell attachment. Carter et al. (*Cell,* 65:599–610, 1991; PCT WO95/06660) describe an epithelial ligand complex called epiligrin found in the extracellular matrix of human keratinocytes. In addition, a 600 kDa basement membrane glycoprotein (BM600) secreted into the culture medium by human keratinocytes (Verrando et al., *Biochim. Biophys. Acta.,* 942:45–56, 1988; Hsi et al., *Placenta* 8:209–217, 1987) is structurally similar to 804G matrix. Although kalinin and epiligrin stimulate adhesion of cells to a substrate, they have not been reported to induce formation of hemidesmosomes.

Any medical device, including indwelling catheters and colostomy tubes, which breach the skin for extended periods of time will result in inflammation and/or infection. It would be particularly desirable to coat the surface of these devices with epithelial cells prior to or after insertion into the skin to prevent these undesirable processes. It would also be desirable to coat surgical meshes with epithelial cells for use in skin allografts. In addition, periodontitis, a severe form of gum disease resulting in destruction of gum tissue epithelium and bone erosion, would be amenable to treatment with dental abutment pieces coated with epithelial cells. This would promote reattachment of detached gum tissue to the tooth surface.

The maintenance of tissues and organs ex vivo is also highly desirable. Tissue replacement therapy is well established in the treatment of human disease. Human epidermal cells can already be grown in vitro and used to populate burn sites and chronic skin ulcers. However, many primary cells and tissues are difficult to establish in vitro on normal tissue culture plastic. Although this problem is partially alleviated by the use of extracellular matrix-coated cell supports, this is only a temporary solution.

Thus, there is a need for trans-epithelial appliances capable of stimulating epithelial cell attachment and spreading and for a composition capable of supporting the viability of tissues and organs maintained ex vivo. The present invention satisfies these needs.

SUMMARY OF THE INVENTION

One embodiment of the present invention is an article of manufacture, comprising:
 a trans-epithelial appliance; and
 a laminin 5 composition deposited on the appliance, with the proviso that the laminin 5 composition is not rat laminin 5.

Preferably, the laminin 5 may be hemidesmosome-inducing laminin 5. Alternatively, the laminin 5 does not induce formation of hemidesmosomes. According to a preferred aspect of this embodiment, the laminin 5 is human laminin 5. Preferably, the laminin 5 is kalinin or epiligrin. Advantageously, the article is an indwelling catheter, needle, metal pin, metal rod, colostomy tube or dental abutment piece. According to one aspect of this preferred embodiment, the article further comprises epithelial cells deposited on the composition. In another aspect of this preferred embodiment, the appliance is used in vivo. Advantageously, the appliance is made of or coated with a biocompatible metal which may be either stainless steel or titanium. Alternatively, the appliance is made of or coated with a ceramic material. This material is preferably hydroxyapatite. According to another aspect of this preferred embodiment, the appliance is made of or coated with a polymer. Advantageously, the polymer is polyester, polyglycolic acid or a polygalactose-polyglycolic acid copolymer.

The present invention also provides a method for inducing epithelial cell attachment to a trans-epithelial appliance, comprising coating the appliance with a laminin 5 composition prior to incubation with epithelial cells, with the proviso that the laminin 5 composition is not rat laminin 5. The laminin 5 may be hemidesmosome-inducing laminin 5. Alternatively, the laminin 5 does not induce formation of hemidesmosomes. According to a preferred aspect of this embodiment, the laminin 5 is human laminin 5. Preferably, the laminin 5 is kalinin or epiligrin. According to another aspect of this embodiment, the appliance is an indwelling catheter, needle, metal pin, metal rod, colostomy tube or dental abutment piece. Preferably, the appliance is made of or coated with a polymer. The polymer may be polyester, polyglycolic acid or a polygalactose-polyglycolic acid copolymer.

Still another embodiment of the invention is a method for inducing epithelial cell attachment to a surface, comprising applying a laminin 5 composition to the surface, with the proviso that the laminin 5 is not rat laminin 5. The laminin 5 may be hemidesmosome-inducing laminin 5. Alternatively, the laminin 5 does not induce formation of hemidesmosomes. According to a preferred aspect of this embodiment, the laminin 5 is human laminin 5. Preferably, the laminin 5 is kalinin or epiligrin.

Another embodiment of the invention is an article of manufacture, comprising:

a biocompatible shaped article adapted for use in vivo in a mammal; and a hemidesmosome formation-inducing laminin 5 composition on the shaped article, with the proviso that the laminin 5 composition is not rat laminin 5.

Preferably, the laminin 5 is human laminin 5.

The present invention also provides a composition for use in growing mammalian epithelial cells, comprising:

laminin 5 protein, wherein the laminin 5 induces the formation of hemidesmosomes in epithelial cells contacting the protein; with the proviso that said laminin 5 is not rat laminin 5; and a pharmaceutically acceptable carrier.

Preferably, the laminin 5 is human laminin 5.

DETAILED DESCRIPTION OF THE INVENTION

The present invention provides shaped articles and transepithelial appliances coated with a soluble or insoluble laminin 5 extracellular matrix molecule produced by various cell types. As defined herein, "laminin 5" refers to the structurally similar laminin-like molecules 804G and NBT-II soluble/insoluble matrix, epiligrin (Carter et al., *Cell,* 65:599–610, 1991; PCT WO95/06660), kalinin (Rouselle et al., *J. Cell Biol.,* 114:567–576, 1991; Burgeson et al., PCT WO92/17498 and PCT WO94/05316) and BM600 (Verrando et al., *Biochim. Biophys. Acta.,* 942:45–56, 1988; Hsi et al., 8:209–217, 1987).

These molecules also promote adhesion of cells cultured thereon and comprise proteins of similar molecular weights to those produced by 804G cells. However, only the 804G and NBT-II matrices induce formation of hemidesmosomes. Thus, laminin 5 may be functionally separated into those molecules which induce formation of hemidesmosomes in epithelial cells cultured thereon and those which do not induce hemidesmosome formation. The enhanced attachment, spreading and hemidesmosome formation of epithelial cells contacted with these molecules will have significant applications in the promotion of cell adhesion in vivo. However, it is contemplated that any laminin 5 will enhance attachment and spreading of epithelial cells subsequently plated on the coated trans-epithelial appliance and will thus be useful in the applications described herein.

The 804G cell line is described by Izumi et al., *Cancer Res.,* (1981) 41:405–409, and was deposited with the American Type Culture Collection, 12301 Parklawn Drive, Rockville, Md., on Feb. 24, 1994, and assigned accession number ATCC CRL 11555. The NBT-II cell line was also deposited on Feb. 24, 1994, and assigned accession number ATCC CRL 11556. All restrictions on the availability to the public of the deposited cells will be irrevocably removed upon the granting of a patent.

The present invention provides both soluble and insoluble laminin 5 proteins, produced by such cells as 804G rat bladder carcinoma cells, NBT-II rat bladder carcinoma cells and human keratinocytes, that can promote cell attachment and spreading in unrelated cells plated on the matrix-coated trans-epithelial appliance. The term "trans-epithelial" appliance indicates any shaped article which penetrates the epithelium. Such appliances include, but are not limited to, dental abutment pieces, needles, metal pins or rods, indwelling catheters, colostomy tubes and surgical meshes made of biocompatible materials.

Epithelial cells may be directly cultured on the laminin 5 deposited by the cells after removal of the cells. Alternatively, the deposited matrix may be solubilized and isolated as described in application Ser. No. 08/324,367. The individual protein components of each laminin 5 may also be isolated or recombinantly produced and used to coat the appliance, either individually or in combination. Alternatively, the conditioned medium from cells can be used to coat the appliance. Alternatively, the purified soluble laminin 5 can be isolated from the conditioned medium and used to coat the appliance. The coating of any desired surface capable of supporting cell adhesion with laminin 5 is within the scope of the present invention.

Methods related to production and isolation of the 804G soluble and insoluble cell matrix are disclosed in copending application Ser. No. 08/324,367 and in U.S. Pat. No. 5,422,264, respectively. The disclosures of both of these documents are hereby incorporated by reference.

Kalinin and epiligrin are present in the conditioned medium of human keratinocytes. The conditioned medium itself may be used as a source of kalinin and epiligrin. Kalinin may be immunopurified from conditioned medium using an immunoaffinity column directed against its BM165 antigen as described by Burgeson et al. (PCT WO92/17498). Epiligrin is also present in the cell matrix secreted by human keratinocytes and may be isolated by a three-step extraction procedure comprising 1% w/v TRITON X-100® to solubilize membrane and cytoplasmic components; 2 M urea and 1 M NaCl to remove nuclear and cytoskeletal components; and 8 M urea to solubilize residual components. 0.5% (w/v) sodium dodecyl sulfate (SDS) is then added and the matrix removed by scraping (Carter et al., *Cell,* 65:599–610, 1991; PCT WO95/06660). It will be appreciated that any soluble or insoluble cell matrix having the ability to support cell adhesion and spreading is within the scope of the present invention.

One major use contemplated for laminin 5 is in cell growth and attachment. A substrate upon which cells are to be grown is coated with laminin 5 or components thereof. The epithelial cells to be grown are then plated on or applied to the desired substrate, and grown on laminin 5 under normal epithelial cell culture conditions. Such cells, including human cells in vivo and in vitro, will grow in an organized, tissue-like fashion on the substrate and will attach and spread. Hemidesmosome formation promoted by the 804G soluble and insoluble matrix is a major advantage, because it greatly enhances cell attachment. It also appears that the organization of cells grown on the 804G matrix is significantly more advanced and tissue-like than control cells.

The substrate used herein may be any desired substrate. For laboratory use, the substrate may be as simple as glass or plastic. For use in vivo, the substrate may be any biologically compatible material capable of supporting cell growth. Suitable substrate materials include shaped articles made of or coated with such materials as collagen, regenerated collagen, polyglycolic acid, polygalactose, polylactic acid or derivatives thereof; biocompatible metals such as titanium and stainless steel; ceramic materials including prosthetic material such as hydroxylapatite; synthetic polymers including polyesters and nylons; polystyrene; polyacrylates; polytetrafluoroethylene and virtually any other material to which biological molecules can readily adhere. The shaped articles contemplated for use in the invention include such forms as sheets, fabrics, prostheses, metal articles, bioerodible articles and implantable articles. The determination of the ability of a particular material to support laminin 5-mediated adhesion and/or hemidesmosome formation will require only routine experimentation by the skilled artisan. Such experimental protocols are disclosed in application Ser. No. 08/324,367. The use of any laminin 5 for coating a shaped article is contemplated, provided that the laminin 5 is capable of inducing hemidesmosome formation in epithelial cells contacted therewith.

One particular use of the present invention is to increase epithelial cell adhesion to target surfaces. For example, prostheses for dental implantation may be coated with laminin 5 to stimulate periodontal cell attachment. These prostheses typically comprise two separate pieces, an implant which is inserted into the bone and an abutment piece which actually contacts the junctional epithelium. Alternatively, the implant and abutment piece may be obtained as a single unit. In a preferred embodiment, the implants and abutment pieces are both made of titanium. Existing teeth may also be similarly coated with the soluble or insoluble matrix as a treatment for gum (junctional epithelium) disease, namely gingivitis and periodontitis, which promote the detachment of the gum from the tooth. These disease conditions allow the accumulation of food and other foreign matter in the space between the gum and the tooth, resulting in infection. Laminin 5 will promote reattachment of the gum to the tooth, thus preventing entry of foreign matter and subsequent infection.

If the substrate is made of a natural or synthetic bioerodible material in the form of a mesh, sheet or fabric, the laminin 5 may be applied directly to the surface thereof or mixed in with the composition. Epithelial cells may then be cultured on the matrix to form transplantable or implantable appliances, including dental abutment pieces, needles, metal pins or rods, indwelling catheters, colostomy tubes, surgical meshes and any other appliance for which coating with the soluble or insoluble matrix is desirable. Alternatively, the materials may be implanted and cells may be permitted to attach in vivo. The epithelial cell-coated surgical meshes will be useful for skin allografts necessitated by compromised skin integrity.

The appliances of the present invention may coated with the complete, active laminin 5 or a structurally and/or functionally equivalent laminin from other cells, and may also be coated with any one of the individual protein components of laminin 5 which will promote cell attachment thereto. The ability of a particular protein component to support these processes will require only routine experimentation by the skilled artisan. Alternatively, the appliance may be coated with the conditioned medium from cells which secrete laminin 5. 804G cells may be grown in 10% fetal calf serum (FCS) or under low serum conditions (about 1% FCS). Additionally, the appliances may be coated with purified laminin 5 which has been secreted by cells into the culture medium.

The appliances may be coated by directly culturing cells thereon and then removing the cells, such that the deposited matrix will remain on the appliance. Alternatively, the cells may be cultured in the laboratory on a conventional plastic or glass substrate, removed, and the deposited matrix obtained by scraping, abrading or treatment with low concentrations (0.5%–1%) of sodium dodecyl sulfate (SDS) or other appropriate detergent.

The recovered matrix is then applied to the appliance. The appliance may be immersed in, incubated in, or sprayed with the conditioned medium from laminin 5-producing cells grown under low or normal serum conditions. The growth of 804G cells under low serum conditions facilitates the purification of the matrix from the medium as described in U.S. Pat. No. 5,422,264. The purified or recombinantly produced laminin 5 may also be applied to the appliance in the same manner as described hereinabove. In a preferred embodiment, the concentration of laminin 5 used for coating the appliance is between about 20 µg/l and about 200 µg/l. In a particularly preferred embodiment, the concentration is between about 50 µg/l and about 150 µg/l.

The 804G conditioned medium may also be used to support tissue and organ growth ex vivo. In human tissue explant culture, 804G matrix is utilized by cells and is incorporated into preexisting basement membranes. For example, in human corneal rims, the soluble laminin variant-containing 804G cell conditioned medium has been used for maintenance of epithelial cell attachment in corneas (Example 9) and induction of assembly of an essential epithelial cell-matrix attachment device in the same tissue.

The corneas may be placed directly in conditioned medium from 804G cells or may be placed in conventional medium supplemented with 804G conditioned medium. The amount of 804G conditioned medium required for optimal corneal maintenance ex vivo will vary depending on the confluency, passage number and particular growth conditions of the cell, although the use of between 10% and 100% conditioned medium (the remainder being normal medium) is contemplated. Optimization of the amount of conditioned medium to use may be determined by one of ordinary skill in the art using routine experimentation. The maintenance of other tissues and organs ex vivo in 804G conditioned medium and 804G conditioned medium-supplemented normal medium is also within the scope of the invention.

Pharmaceutical preparations of laminin 5 or its active components can be prepared in any suitable form, and generally comprise the active ingredient in combination with any of the well known pharmaceutically acceptable carriers. The carriers can be injectable carriers, topical carriers, transdermal carriers, and the like. The preparation may advantageously be in a form for topical administration, such as an ointment, gel, cream, spray, dispersion, suspension or paste. The preparations may further advantageously include preservatives, antibacterials, antifungals, antioxidants, osmotic agents, and similar materials in composition and quantity as is conventional. For assistance in formulating the compositions of the present invention, one may refer to Remington's Pharmaceutical Sciences, 15th Ed., Mack Publishing Co., Easton, Pa. (1975).

As described in application Ser. No. 08/324,367, SCC12 human keratinocytes, normally unable to themselves form hemidesmosomes, were induced to form these structures when plated on the 804G extracellular matrix. Normal human keratinocytes (derived from human foreskins), HaCaT (immortalized cells), and SCC13 cells also exhibited almost identical responses when grown on the 804G matrix in comparison to the SCC12 cells. In each of these cell types, growth on the 804G matrix led to a redistribution of integrins and mature hemidesmosome formation.

In addition, similar experiments have been performed on the matrix produced by the NBT-II cell line. The results from these experiments are virtually identical to those illustrated for the 804G matrix. Cells grown on NBT-II matrix were stimulated to form mature hemidesmosomes and redistribute intracellular integrins.

Clones corresponding to 804G matrix polypeptides were isolated as described below.

EXAMPLE 1

Isolation of Clones Corresponding to 804G Matrix Polypeptides

A human keratinocyte lambda gt11 expression library (Clontech, Inc., Palo Alto, Calif.) was screened with an 804G matrix polyclonal antiserum according to Huynh et al., (*DNA Cloning: A Practical Approach*, Volume I, D. Glover, Ed., IRL Press, Oxford, 1985). This polyclonal antiserum is described in application Ser. No. 08/324,367. Antibodies absorbed by the fusion protein products of the two clones showed reactivity with the 140 kD and 100 kD molecular weight species in an 804G matrix preparation and a whole cell extract of SCC12 cells. The antiserum was also used to screen a rat 804G expression library. Two independent clones from which antibodies to the 140 kD/100 kD polypeptide components were epitope-selected revealed over 85% identity with stretches of 94 residues in domain IV and 86 residues in domain I/II of a recently identified variant of the B2 chain of laminin that has been termed laminin B2t (Kallunki et al., (1992) *J. Cell Biol.*, 119:679–685). The B2t variant is not contained in EHS laminin, and therefore represents a new subunit. In addition, five clones from which antibodies to the rat 150 kD component were epitope-selected were isolated.

To further characterize positive clones, plaque lifts of nitrocellulose-bound fusion proteins were used to epitope select antibodies (Sambrook et al., (1989) *Molecular Cloning: A Laboratory Manual*, 2nd ed., Cold Spring Harbor laboratory Press, Cold Spring Harbor, N.Y.). cDNA inserts were subcloned into M13 vectors and sequenced by the dideoxy chain termination method (Sanger et al., (1977) *Proc. Natl. Acad. Sci. USA*, 74:5463–5467). Sequence analyses were performed using the GCG sequence analysis software package (University of Wisconsin Biotechnology Center, Madison, Wis.).

The nucleotide sequence of the 140 kDa clone revealed that it encoded a region spanning amino acids 550–810 in domain I/II of human laminin B2t. This experiment illustrates the cross-reactivity of the matrix associated polypeptides with the laminin B2t variant. The 150 kD clones encoded regions exhibiting sequence similarity to the Drosophila laminin A chain (Garrison et al., (1991) *J. Biol. Chem.*, 266:22899–22904). The overall sequence identity between 294 amino acids of the rat 150 kD sequence (SEQ ID NO: 1) and amino acid residues 2365–2724 of the Drosophila laminin A chain (SEQ ID NO: 2) was 25%, a significant overlap considering the evolutionary difference between rat and Drosophila. SEQ ID NO: 1 also exhibited 21% identity to amino acids 1634–1970 of human merosin (SEQ ID NO: 3), a laminin A isoform.

The cDNA sequences encoding these protein components may be inserted into either conventional prokaryotic or eukaryotic expression vectors, widely available from many commercial sources including Stratagene (La Jolla, Calif.), Invitrogen (San Diego, Calif.) and Promega (Madison, Wis.) using routine techniques, transfected into cells, and the expressed protein purified according to well known methods.

EXAMPLE 2

Adhesion of Epithelial Cells to 804G Soluble Matrix-Coated Dental Implants

The three types of titanium implants used were: IMZ titanium plasma sprayed (Interpore International, Irvine, Calif.), HA-coated titanium implant (Calcitek, Carlsbad, Calif.), and a screw-vent titanium implant (Dentsply, Inc., Encino, Calif.). The implant from Interpore had a polished titanium collar that was not covered with the sprayed titanium and the Calcitek implant came with a polished titanium healing screw.

The implants were thoroughly cleaned with a detergent solution, extensively rinsed with tap water followed by deionized water and allowed to dry. Implants were sterilized by immersion in 95% ethanol, rinsed in sterile PBS lacking calcium and magnesium (BioWhittaker, Walkersville, Md.) and air-dried in a sterile petri dish.

One sample of each type of implant was left untreated, one was coated with 804G culture medium which contains the soluble matrix (See U.S. Pat. No. 5,422,264) (DMEMC= DMEM containing 10% fetal bovine serum, 2 mM glutamine, 100 units/ml penicillin and 100 μg/ml streptomycin), and one was coated with 804G conditioned medium collected after four days of cell growth. Coating was performed by placing the implants into sterile 0.65 ml tubes containing DMEMC, 100 μl 804G conditioned medium, or nothing (untreated control). The implants were placed into the solutions upside down to ensure coating of the exposed polished titanium on the Interpore and Calcitek implants. The samples were then placed at 4° C. overnight (about 16 hours). The implants were removed form the coating solutions and placed into six well tissue culture plates, one implant per well. Nonspecific binding sites on each implant were blocked with 5 ml of 1% (w/v) bovine serum albumin (BSA) in PBS for 5 hours at room temperature. The blocking solution was removed and the implants were washed three times with PBS.

FGmet2 human pancreatic carcinoma cells, an epithelial cell line, were used to test for rapid cell adhesion to the coated implants. The cells were trypsinized and centrifuged at 1500 rpm for 5 minutes. The cell pellet was washed twice by resuspension in 1% BSA in DMEM and centrifuged. The cell pellet was resuspended in 1% BSA in DMEM to a final concentration of $2.2 \times 10^6$ cells/ml. The six well plates were tilted to allow the implants to rest against one edge of the well and the implants were overlayed with 1 ml of the cell suspension. The cells were incubated with the implants for 30 min at 37° C., removed by aspiration, and the implants washed three times with PBS. The cells were fixed for 5 minutes with 3% paraformaldehyde in 2% sucrose and PBS, and stained for 15 minutes with 0.5% crystal violet in 20% methanol. The excess dye was removed by rinsing under tap water and the implants were examined using an inverted phase microscope.

Significant FGmet2 cell attachment and spreading was observed only on the implants coated with the 804G conditioned medium. This result indicates that a hemidesmosome formation-inducing matrix secreted by 804G cells can induce epithelial cell attachment and spreading on a shaped, trans-epithelial appliance.

EXAMPLE 3

The experiment described in Example 2 is repeated, substituting kalinin or epiligrin in place of the 804G conditioned medium. Similar results are obtained.

The ability of soluble 804G matrix to coat absorbable and nonabsorbable surgical meshes and the subsequent ability of the matrix to support rapid adhesion and cell proliferation was assessed as described in the following two examples.

EXAMPLE 4

Rapid Adhesion of Epithelial Cells to a Surgical Mesh 804G conditioned medium was used as a source of soluble matrix protein. A small piece of polypropylene (PROLENE™), polyester (MERSILENE™), and polyglactin (Vicryl™, a biodegradable copolymer comprising 90% glycolide, a polyglycolic acid derivative and 10% glactide, a polygalactose derivative) mesh (all from Ethicon, Inc.) were each placed into wells of a 24 well tissue culture plate containing either 1 ml 804G conditioned medium or 1 ml DMEM complete medium and incubated overnight at 4° C. The meshes were washed twice with PBS containing 1% BSA (PBS+BSA) and nonspecific binding sites were blocked with PBS+BSA for one hour at room temperature. $4 \times 10^5$ FGmet2 cells in 1 ml DMEM+1% BSA+25 mM HEPES were pipetted on top of the meshes and allowed to incubate at 37° C. for 35 min. The meshes were then transferred into a 6 well tissue culture plate and washed three times for 5 min each in 5 ml PBS. The meshes were fixed in 1 ml 3% paraformaldehyde+2% sucrose in PBS for 5 min at room temperature and the adherent cells stained with 0.5% crystal violet in 20% methanol for 15 min at room temperature. The meshes were washed extensively with water to remove nonspecific staining.

The results indicated that both the 804G-treated Mersilene™ and Vicryl™ meshes visibly stained darker than the control-treated meshes. Thus, the polyester and polyglactin 910 meshes supported 804G matrix adhesion and, more importantly, promoted rapid adhesion of epithelial cells to these materials. In contrast, no detectable cell staining was observed with the 804G-treated Prolene™ mesh which is consistent with the observation that polypropylene has a low capacity for binding proteins.

EXAMPLE 5

The experiment described in Example 4 is repeated, substituting kalinin or epiligrin in place of the 804G soluble matrix. Similar results are obtained.

EXAMPLE 6

Growth of Epithelial Cells on Soluble 804G Matrix-Precoated Surgical Meshes

Mersilene™ and Vicryl™ meshes were precoated in 1 ml degassed 804G conditioned medium or degassed DMEM complete media containing 25 mM HEPES overnight at 4° C. Both mediums were degassed for 30 min at room temperature with a vane pump drawing a 23 mm Hg vacuum. The meshes were washed twice with sterile PBS and 1 ml RPMI complete medium containing $8 \times 10^4$ FGmet2 epithelial cells was pipetted on top of the meshes and allowed to incubate at 37° C.

After one day of growth, FGmet2 cells were visibly attached and spreading on 804G-treated meshes. The loose weave of the Mersilene™ mesh permitted better visualization of the cells than the tight weave of the Vicryl™ mesh. After two days the meshes were transferred to a new plate, fresh medium was added and the incubation was continued. After five days, cells were growing extensively along the Mersilene™ mesh fibers and appeared to cover more than 50% of the fiber surface. In contrast, cells growing on the control-treated mesh grew into a ball-shaped structure and did not exhibit significant growth along the fiber surface. These results demonstrate the unique ability of the soluble 804G matrix to adsorb onto medically important surfaces and promote the attachment and proliferation of cells on these materials.

EXAMPLE 7

The experiment described in Example 6 is repeated, substituting kalinin or epiligrin in place of the soluble 804G matrix. Similar results are obtained.

EXAMPLE 8

Preservation of Corneal Explants with 804G Soluble Matrix

Human donor corneal rims procured following penetrating keratoplasties were maintained in DMEM containing FCS (DMEM−) or in the same medium supplemented with soluble 804G matrix, including adhesion complex-associated matrix components, that are secreted in large amounts by 804G cells (DMEM+). After 72 hours, the tissue was processed for electron and immunofluorescence microscopy using various adhesion complex antibodies.

The epithelial layers became detached from the underlying stroma in corneal rims maintained in DMEM−. This detachment was correlated with a loss of adhesion complexes and their protein constituents. In contrast, after 72 hours in DMEM+, the epithelial layers appear healthy with numerous adhesion complexes in regions of cell-stromal attachment. In this wound model, no morphologic hemidesmosomes were observed in epithelial cells repopulating "wounds" in tissue material maintained in DMEM−. However, in DMEM+ media, morphologic hemidesmosomes were seen along the bare stroma in areas of epithelial cell-wound bed interaction.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method for promoting adhesion of periodontal tissue affected with periodontitis or gingivitis to a prosthetic appliance, comprising the steps of:

applying a composition comprising laminin 5 to said appliance, wherein said laminin 5 is not rat laminin 5; and contacting said periodontal tissue with said appliance.

2. The method of claim 1, wherein said laminin 5 is human laminin 5.

3. The method of claim 1, wherein said laminin 5 is obtained by recombinant methods.

4. The method of claim 1, further comprising depositing epithelial cells on said laminin 5 composition prior to contacting said periodontal tissue with said appliance.

5. The method of claim 1, wherein said periodontal tissue is gingival tissue or gum junctional epithelium.

6. A method for treating periodontitis or gingivitis, comprising the step of applying a composition comprising laminin 5 to the surface of a tooth in an area affected with periodontitis or gingivitis, wherein said laminin 5 is not rat laminin 5.

7. The method of claim 6, wherein said laminin 5 is human laminin 5.

8. The method of claim 6, wherein said laminin 5 is obtained by recombinant methods.

9. The method of claim 6, further comprising depositing epithelial cells on said composition.

10. The method of claim 6, wherein said periodontal tissue is gingival tissue or gum junctional epithelium.

* * * * *